(12) United States Patent
Wu et al.

(10) Patent No.: US 10,542,899 B2
(45) Date of Patent: *Jan. 28, 2020

(54) CATHETER HAVING CLOSED LOOP ARRAY WITH IN-PLANE LINEAR ELECTRODE PORTION

(71) Applicant: BIOSENSE WEBSTER (ISRAEL) LTD., Yokneam (IL)

(72) Inventors: Steven Wu, San Jose, CA (US); Sungwoo Min, Fullerton, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/017,298

(22) Filed: Jun. 25, 2018

(65) Prior Publication Data

US 2018/0303361 A1    Oct. 25, 2018

Related U.S. Application Data

(63) Continuation of application No. 14/754,553, filed on Jun. 29, 2015.

(51) Int. Cl.
| | |
|---|---|
| *A61B 5/042* | (2006.01) |
| *A61B 18/14* | (2006.01) |
| *A61B 5/00* | (2006.01) |
| *A61B 18/00* | (2006.01) |

(52) U.S. Cl.
CPC ............ *A61B 5/0422* (2013.01); *A61B 5/042* (2013.01); *A61B 5/6852* (2013.01); *A61B 5/6859* (2013.01); *A61B 18/1492* (2013.01); *A61B 2018/0016* (2013.01);

(Continued)

(58) Field of Classification Search
CPC ...... A61N 1/05; A61B 5/0422; A61B 18/1492
See application file for complete search history.

(56) References Cited

U.S. PATENT DOCUMENTS

| | | | |
|---|---|---|---|
| 4,529,912 A | 6/1985 | Gelinas et al. | |
| 5,702,438 A | 12/1997 | Avitall | |
| 5,964,757 A | 10/1999 | Ponzi | |

(Continued)

FOREIGN PATENT DOCUMENTS

| | | |
|---|---|---|
| AU | 2015202258 A1 | 5/2015 |
| AU | 2016204351 A1 | 1/2017 |

(Continued)

OTHER PUBLICATIONS

European Examination Report in corresponding European Application No. 15195293.4, dated Jan. 19, 2017, 6 pages.

(Continued)

*Primary Examiner* — Lee S Cohen
(74) *Attorney, Agent, or Firm* — Roberts Mlotkowski Safran Cole & Calderon, P.C.

(57) ABSTRACT

A catheter adapted or high density mapping and/or ablation of tissue surface has a distal electrode array with offset spine loops, each spine loop having at least a pair of linear portions and a distal portion connecting the pair of linear portions, and one or more electrodes on each linear portion. The linear portions of the plurality of offset spine loops are arranged in-plane a single common plane, and the distal portions of the plurality of offset spine loops are arranged off-plane from the single common plane.

18 Claims, 13 Drawing Sheets

(52) U.S. Cl.
CPC ............... *A61B 2018/00267* (2013.01); *A61B 2018/00577* (2013.01); *A61B 2018/1407* (2013.01)

(56) References Cited

U.S. PATENT DOCUMENTS

| | | | |
|---|---|---|---|
| 6,029,091 A | 2/2000 | De La Rama et al. |
| 6,071,280 A | 6/2000 | Edwards et al. |
| 6,071,282 A | 6/2000 | Fleischman |
| 6,123,699 A | 9/2000 | Webster, Jr. |
| 6,171,277 B1 | 1/2001 | Ponzi |
| 6,183,435 B1 | 2/2001 | Bumbalough et al. |
| 6,183,463 B1 | 2/2001 | Webster, Jr. |
| 6,198,974 B1 | 3/2001 | Webster, Jr. |
| 6,210,407 B1 | 4/2001 | Webster |
| 6,267,746 B1 | 7/2001 | Bumbalough |
| 6,415,187 B1 | 7/2002 | Kuzma et al. |
| 6,522,932 B1 | 2/2003 | Kuzma et al. |
| 6,652,515 B1 | 11/2003 | Maguire et al. |
| 6,658,302 B1 | 12/2003 | Kuzma et al. |
| 6,961,602 B2 | 11/2005 | Fuimaono et al. |
| 7,027,851 B2 | 4/2006 | Mejia |
| 7,089,045 B2 | 8/2006 | Fuimaono et al. |
| 7,099,712 B2 | 8/2006 | Fuimaono et al. |
| 7,228,164 B2 | 6/2007 | Fuimaono et al. |
| 7,257,435 B2 | 8/2007 | Plaza |
| 7,412,274 B2 | 8/2008 | Mejia |
| 7,429,261 B2 | 9/2008 | Kunis et al. |
| 7,561,907 B2 | 7/2009 | Fuimaono et al. |
| 8,271,099 B1 | 9/2012 | Swanson |
| 8,391,947 B2 | 3/2013 | Urman et al. |
| 8,486,063 B2 | 7/2013 | Werneth et al. |
| 8,565,894 B2 | 10/2013 | Vetter et al. |
| 8,603,069 B2 | 12/2013 | Selkee |
| 8,744,599 B2 | 6/2014 | Tegg |
| 9,044,245 B2 | 6/2015 | Condie et al. |
| 9,820,664 B2 | 11/2017 | Hoitink et al. |
| 9,833,608 B2 | 12/2017 | Masson |
| 9,907,480 B2 | 3/2018 | Basu et al. |
| 2005/0159741 A1 | 7/2005 | Paul et al. |
| 2009/0198300 A1 | 8/2009 | Zhang et al. |
| 2011/0118726 A1 | 5/2011 | De La Rama et al. |
| 2012/0271302 A1 | 10/2012 | Behl et al. |
| 2012/0296232 A1 | 11/2012 | Ng |
| 2013/0253504 A1* | 9/2013 | Fang .................. A61B 18/1492 606/41 |
| 2013/0274582 A1 | 10/2013 | Afonso et al. |
| 2014/0200639 A1 | 7/2014 | De La Rama |
| 2014/0296902 A1 | 10/2014 | Huszar et al. |
| 2014/0316496 A1 | 10/2014 | Masson et al. |
| 2014/0350564 A1 | 11/2014 | Huszar et al. |
| 2015/0105645 A1 | 4/2015 | Subramaniam et al. |
| 2015/0141785 A1 | 5/2015 | Hayam et al. |
| 2015/0351652 A1 | 12/2015 | Marecki et al. |
| 2015/0374252 A1 | 12/2015 | De La Rama et al. |
| 2016/0143588 A1* | 5/2016 | Hoitink .............. A61B 5/6858 600/374 |
| 2016/0213916 A1 | 7/2016 | De La Rama |
| 2016/0317094 A1 | 11/2016 | Byrd et al. |
| 2016/0331471 A1* | 11/2016 | Deno .................... A61B 34/20 |
| 2016/0374582 A1 | 12/2016 | Wu et al. |
| 2016/0374753 A1 | 12/2016 | Wu et al. |
| 2017/0000365 A1 | 1/2017 | Wu et al. |
| 2017/0042449 A1 | 2/2017 | Deno et al. |
| 2017/0049348 A1 | 2/2017 | Deno et al. |
| 2017/0112404 A1 | 4/2017 | De La Rama et al. |
| 2017/0112405 A1 | 4/2017 | Sterrett et al. |
| 2017/0319269 A1 | 11/2017 | Oliverius et al. |
| 2017/0367756 A1 | 12/2017 | Sliwa et al. |
| 2018/0050190 A1 | 2/2018 | Masson |
| 2018/0070845 A1 | 3/2018 | Hoitink et al. |
| 2018/0116539 A1 | 5/2018 | Olson et al. |

FOREIGN PATENT DOCUMENTS

| | | |
|---|---|---|
| AU | 2016204353 A1 | 1/2017 |
| AU | 2016204355 A1 | 1/2017 |
| CA | 2934209 A1 | 12/2016 |
| CA | 2934211 A1 | 12/2016 |
| CA | 2934214 A1 | 12/2016 |
| CN | 101797181 A | 8/2010 |
| CN | 105960201 A | 9/2016 |
| CN | 106264715 A | 1/2017 |
| CN | 106264716 A | 1/2017 |
| CN | 106308790 A | 1/2017 |
| EP | 2664295 A1 | 11/2013 |
| EP | 2 732 843 A1 | 5/2014 |
| EP | 2752153 A1 | 7/2014 |
| EP | 2907462 A1 | 8/2015 |
| EP | 3023052 A1 | 5/2016 |
| EP | 3111871 A1 | 1/2017 |
| EP | 3111872 A1 | 1/2017 |
| EP | 3114987 A1 | 1/2017 |
| IN | 201614021431 A | 12/2016 |
| IN | 201614021432 A | 12/2016 |
| IN | 201614021450 A | 12/2016 |
| JP | 2017012750 A | 1/2017 |
| JP | 2017012755 A | 1/2017 |
| JP | 2017038919 A | 2/2017 |
| RU | 2016124794 A | 12/2017 |
| RU | 2016124801 A | 12/2017 |
| RU | 2016125763 A | 1/2018 |
| WO | 2014113612 A1 | 7/2014 |
| WO | 2015057521 A1 | 4/2015 |
| WO | 2015095577 A1 | 6/2015 |
| WO | 2015130824 A1 | 9/2015 |
| WO | 2016001015 A1 | 1/2016 |

OTHER PUBLICATIONS

Extended European Search Report for European Application No. 15195293.4, dated Apr. 12, 2016, 5 pages.
Extended European Search Report for European Application No. 16176559.9, dated Nov. 7, 2016, 6 pages.
Extended European Search Report for European Application No. 16176598.7, dated Nov. 7, 2016, 4 pages.
Extended European Search Report for European Application No. 16176803.1, dated Dec. 12, 2016, 5 pages.
Extended European Search Report for European Application No. 18166678, dated Jun. 28, 2018, 8 pages.
Israeli Patent Application No. 246414, filed on Jun. 23, 2016, 2 pages (English Abstract attached—also corresponds to US20160374753).
Israeli Patent Application No. 246415, filed on Jun. 23, 2016, 2 pages (English Abstract attached—also corresponds to US20160374582).
Israeli Patent Application No. 246416, filed on Jun. 23, 2016, 2 pages (English Abstract attached—also corresponds to US20170000365).
Office Action for European Application No. 15195293.4, dated Jul. 20, 2017, 5 pages.
Extended European Search Report for Application No. 19164969.8 dated Jul. 19, 2019, 11 pages.

\* cited by examiner

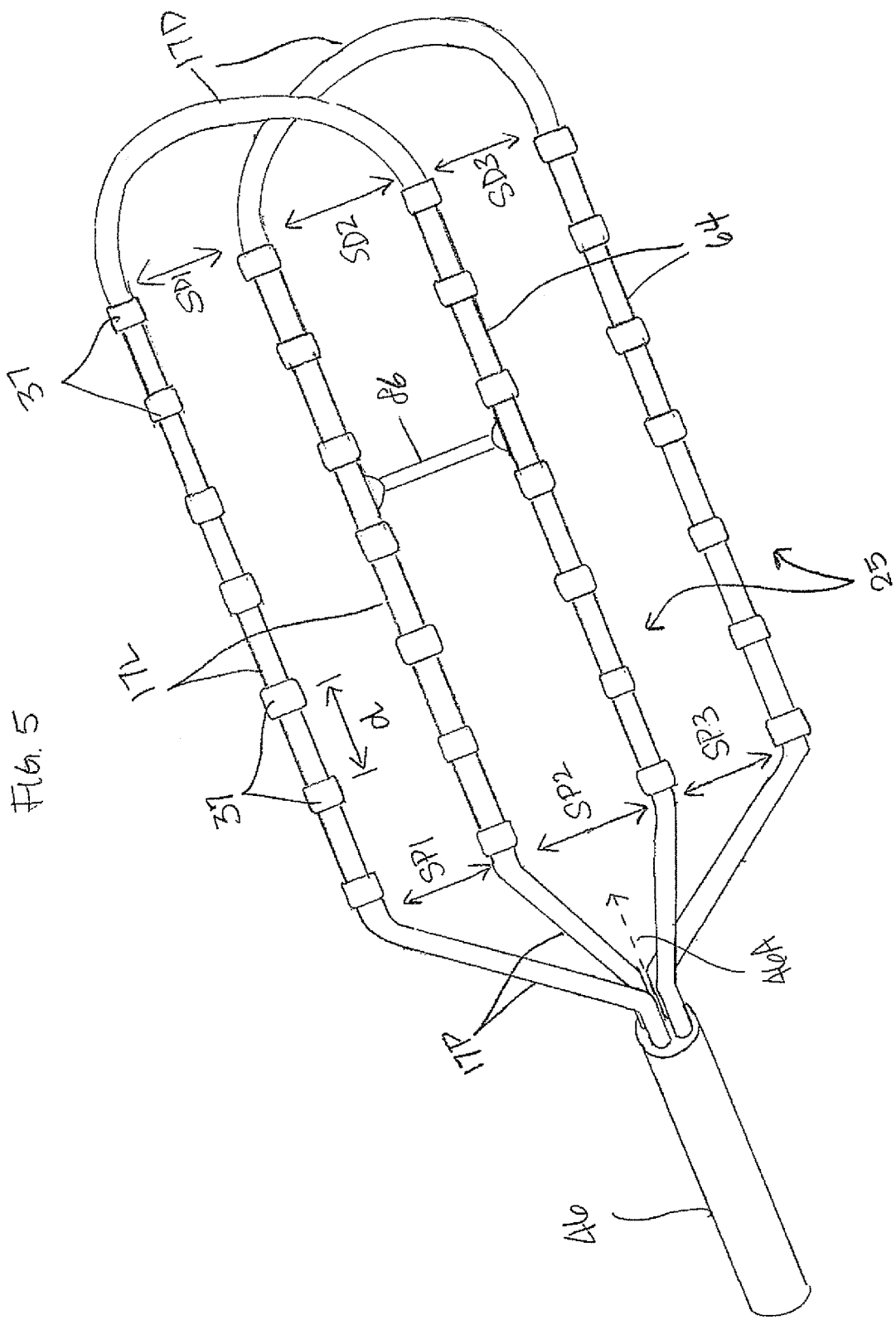

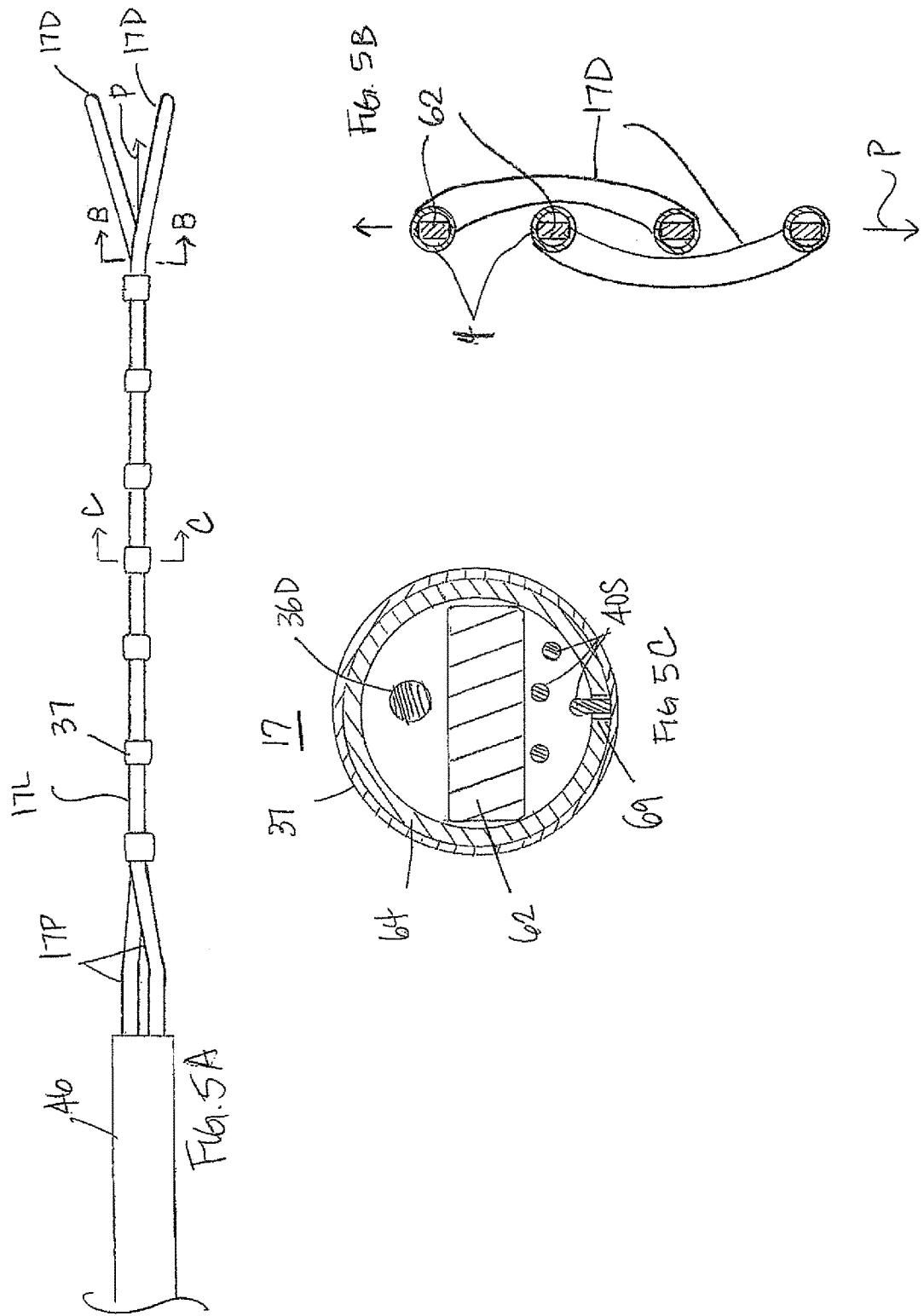

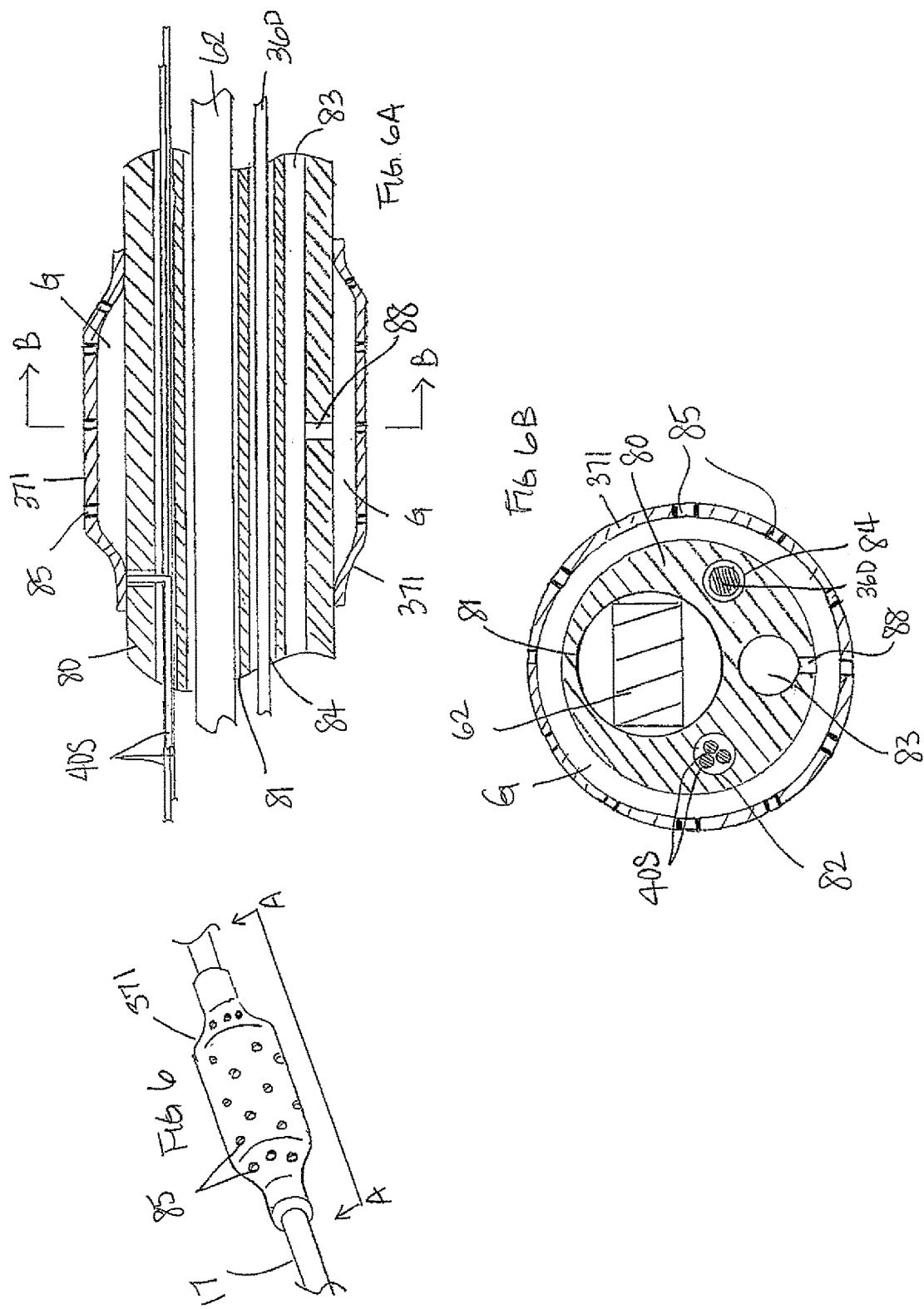

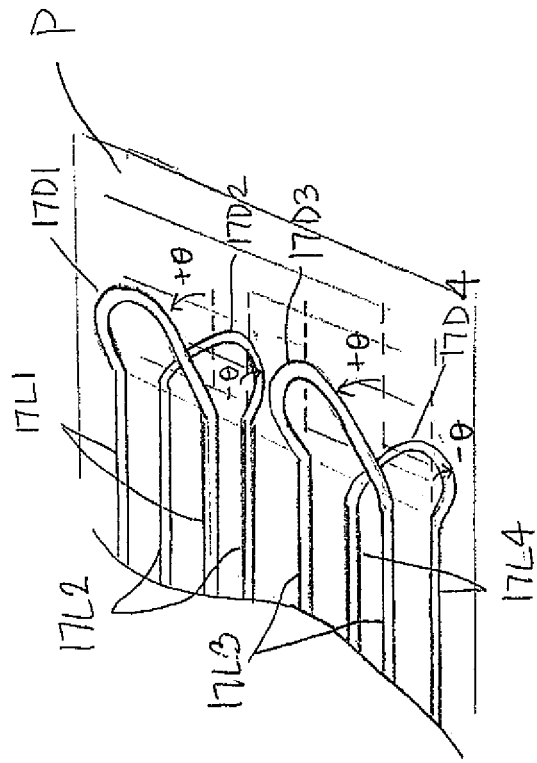
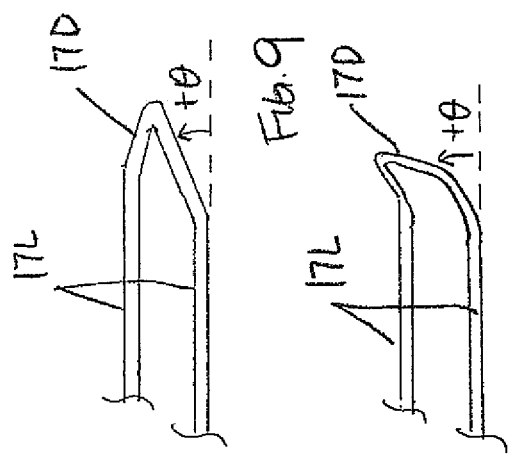

CATHETER HAVING CLOSED LOOP ARRAY WITH IN-PLANE LINEAR ELECTRODE PORTION

CROSS-REFERENCE TO RELATED APPLICATIONS

This application is a continuation of U.S. patent application Ser. No. 14/754,553, filed Jun. 29, 2015, the entire contents of which are incorporated herein by reference.

FIELD OF INVENTION

This invention relates to catheters, in particular, intravascular catheters for tissue diagnostics and ablation.

BACKGROUND

Cardiac arrhythmia, such as atrial fibrillation, occurs when regions of cardiac tissue abnormally conduct electric signals to adjacent tissue, thereby disrupting the normal cardiac cycle and causing asynchronous rhythm. Important sources of undesired signals are located in the tissue region, for example, one of the atria or one of the ventricles. Regardless of the sources, unwanted signals are conducted elsewhere through heart tissue where they can initiate or continue arrhythmia.

Procedures for treating arrhythmia include surgically disrupting the origin of the signals causing the arrhythmia, as well as disrupting the conducting pathway for such signals. More recently, it has been found that by mapping the electrical properties of the endocardium and the heart volume, and selectively ablating cardiac tissue by application of energy, it is possible to cease or modify the propagation of unwanted electrical signals from one portion of the heart to another. The ablation process destroys the unwanted electrical pathways by formation of non-conducting lesions.

In this two-step procedure—mapping followed by ablation—electrical activity at points in the heart is typically sensed and measured by advancing a catheter containing one or more electrical sensors into the heart, and acquiring data at a multiplicity of points. These data are then utilized to select the target areas at which ablation is to be performed.

For greater mapping resolution, it is desirable for a mapping catheter to provide very high density signal maps through the use of a multitude of electrodes sensing electrical activity within a small area, for example, about a square centimeter. For mapping within an atria or a ventricle (for example, an apex of a ventricle), it is desirable for a catheter to collect larger amounts of data signals within shorter time spans. It is also desirable for such a catheter to be adaptable to different tissue surfaces, for example, flat, curved, irregular or nonplanar surface tissue, yet remain in a predetermined configuration where electrode spatial relationships are generally maintained during sensing and mapping.

SUMMARY OF THE INVENTION

The catheter of the present invention is intended to enable high density mapping and/or ablation of tissue surface, with a distal electrode array having a plurality of closed spine loops that are laterally offset from each other. Advantageously, the spine loops have electrode-carrying main portions and distal connecting portions, where the electrode-carrying main portions are arranged in a common plane ("in-plane"), with a predetermined configuration that is generally maintained by the distal connecting portions which are off-plane and noninterfering with the in-plane arrangement of the electrode-carrying portions. The in-plane arrangement of the spine loops maximizes electrode-to-tissue contact for high density mapping signals while the predetermined configuration provides greater regularity, consistency and predictability in electrode placement on the tissue surface.

The predetermined configuration includes one or more spatial relationships between adjacent spine loops and/or adjacent electrodes on adjacent spine loops. For example, the electrode-carrying main portions of the spine loops may be linear and parallel to each other such that a consistent spacing is provided and maintained between adjacent electrodes during use of the catheter for electrophysiologic procedures, including, pacing, ECG reading, and the like).

In some embodiments, the catheter includes an elongated catheter body and a distal electrode array comprising a plurality of offset spine loops, with each spine loop having at least a pair of electrode-carrying portions and a distal portion connecting the pair of electrode-carrying portions, wherein the electrode-carrying portions of the offset spine loops are arranged in-plane in a single common plane, and the distal portions of the offset spine loops are arranged off-plane from the single common plane.

In some embodiments, the electrode-carrying portions of the offset spine loops are linear. The electrode-carrying portions of the offset spine loops may be parallel to each other. The distal portions may be nonlinear, for example, curved or angularly shaped with corners.

In some embodiments, the offset configuration of the spine loops includes at least one electrode-carrying portion of each spine loop being positioned between electrode-carrying portions of one or more different spine loops.

In some embodiments, the offset configuration of the spine loops includes the pair of electrode-carrying portions of each spine loop being separated therebetween by at least an electrode-carrying portion of a different spine loop.

In some embodiments, the distal portions of adjacent spine loops are angled oppositely off-plane from each other so as to remain noninterfering with the in-plane arrangement of the electrode-carrying portions.

In additional embodiments, the catheter includes an elongated catheter body, a distal electrode array comprising a plurality of offset spine loops, with each spine loop having at least a pair of linear portions and a distal portion connecting the pair of linear portions, wherein the linear portions of the offset spine loops are arranged in-plane in a single common plane, and the distal portions of the plurality of offset spine loops are arranged off-plane from the single common plane.

In some embodiments, the linear portions of the offset spine loops are parallel to each other and the distal portions are nonlinear.

In some embodiments, the offset arrangement of the spine loops includes at least one linear portion of each spine loop being positioned between linear portions of one or more different spine loops.

In some embodiments, the offset arrangement of the spine loops includes the pair of linear portions of each spine loop being separated therebetween by at least a linear portion of a different spine loop.

In some embodiments, the distal portions of adjacent spine loops are angled oppositely off-plane from each other.

A catheter of the present invention may also include one or more space members extending between at least two adjacent linear portions to help maintain the predetermined configuration and/or spatial relationship(s).

BRIEF DESCRIPTION OF THE DRAWINGS

These and other features and advantages of the present invention will be better understood by reference to the following detailed description when considered in conjunction with the accompanying drawings wherein:

FIG. 5 is a perspective view of a distal electrode assembly of FIG. 1.

FIG. 5A is a side view of the distal electrode assembly of FIG. 5.

FIG. 5B is an end view of the distal electrode assembly of FIG. 5A, taken along line B-B.

FIG. 5C is an end view of a spine loop of FIG. 5A, taken along line C-C.

FIG. 6 is a detailed perspective view of an irrigated ring electrode on a spine loop, in accordance with some embodiments.

FIG. 6A is a side cross-sectional view of the irrigated ring electrode of FIG. 6, taken along line A-A.

FIG. 6B is an end cross-sectional view of the irrigated ring electrode of FIG. 6A, taken along line B-B.

FIG. 7 is partial perspective view of a distal electrode assembly, in accordance with another embodiment.

FIG. 8 is a partial perspective view of a spine loop, in accordance with another embodiment.

FIG. 9 is a partial perspective view of a spine loop, in accordance with another embodiment.

DETAILED DESCRIPTION OF THE INVENTION

Figure 1:
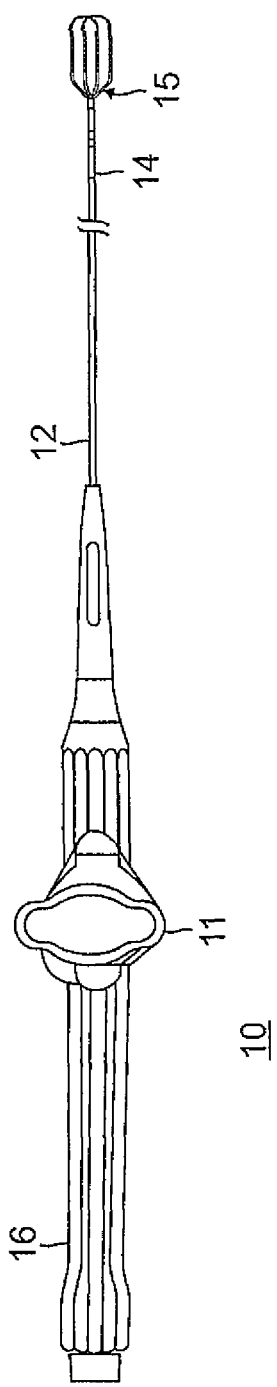
FIG. 1 is a perspective view of a catheter of the present invention, in accordance with some embodiments.

As shown in FIG. 1, the catheter 10 comprises an elongated catheter body 12, an intermediate deflection section 14, a distal electrode assembly or array 15, and a deflection control handle 16 attached to the proximal end of the catheter body 12. In accordance with a feature of the present invention, the distal electrode array 15 has a plurality of closed offset spine loops 17 whose electrode-carrying portions lie within a common plane.

Figure 2A:
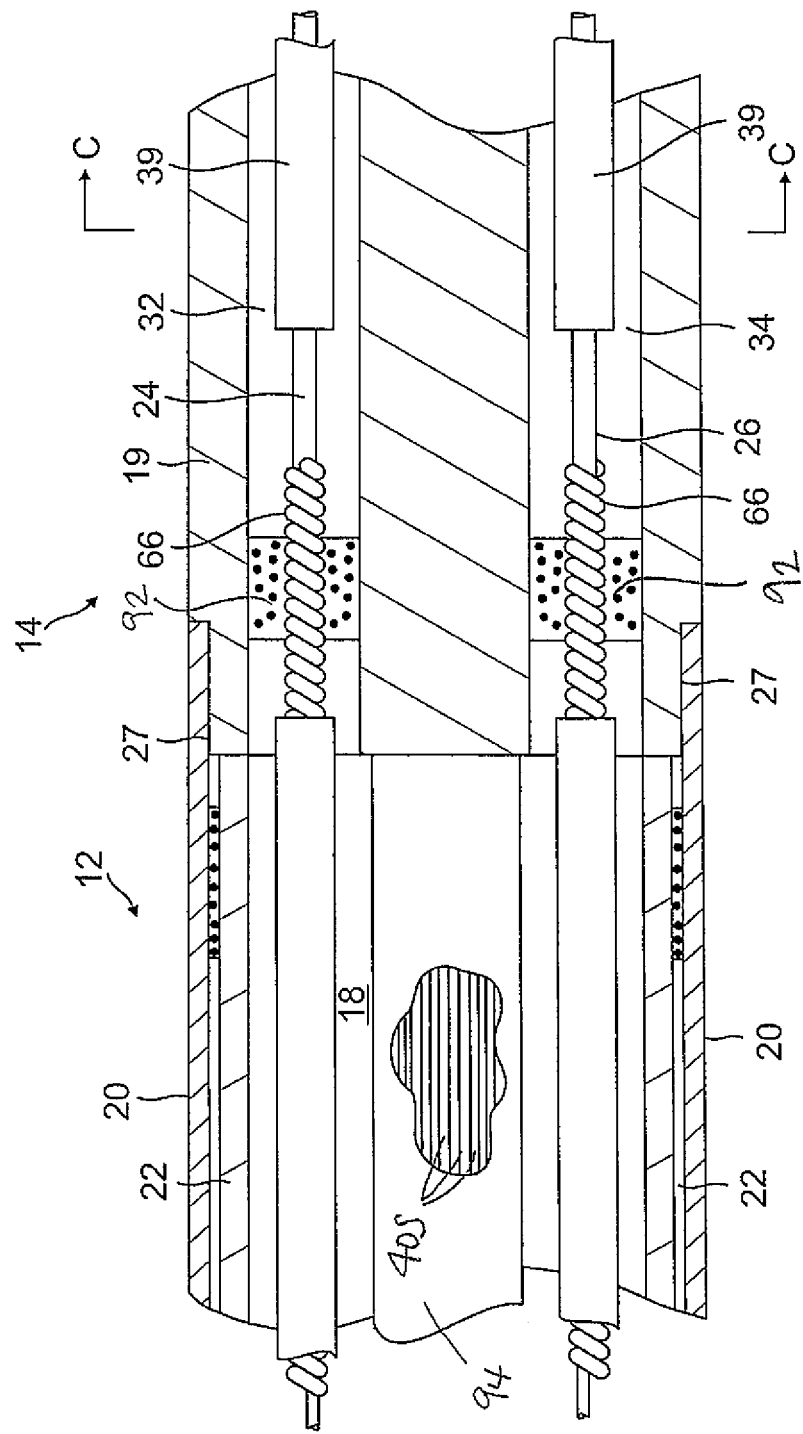
FIG. 2A is a side cross-sectional view of the catheter of FIG. 1, including a junction between a catheter body and a deflection section, taken along a first diameter.
Figure 2B:
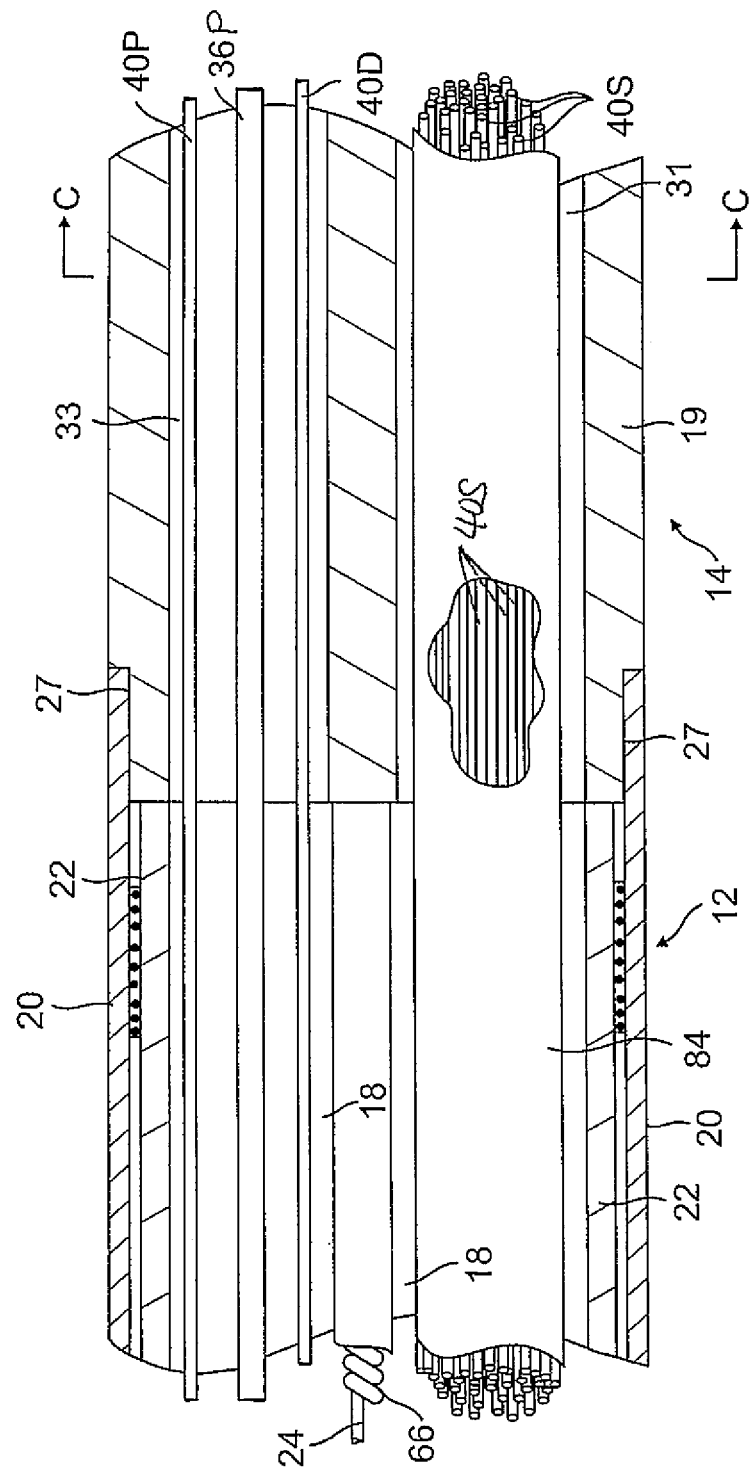
FIG. 2B is a side cross-sectional view of the catheter of FIG. 1, including the junction of FIG. 2A, taken along a second diameter generally perpendicular to the first diameter.

With reference to FIGS. 2A and 2B, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. In some embodiments, the catheter body 12 comprises an outer wall 20 made of polyurethane or PEBAX. The outer wall 20 comprises an imbedded braided mesh of stainless steel or the like to increase torsional stiffness of the catheter body 12 so that, when the control handle 16 is rotated, the intermediate section 14 of the catheter 10 rotates in a corresponding manner.

The outer diameter of the catheter body 12 is not critical. Likewise, the thickness of the outer wall 20 is not critical, but is thin enough so that the central lumen 18 can accommodate a puller wire, one or more lead wires, and any other desired wires, cables or tubes. If desired, the inner surface of the outer wall 20 is lined with a stiffening tube 22 to provide improved torsional stability.

Figure 2C:
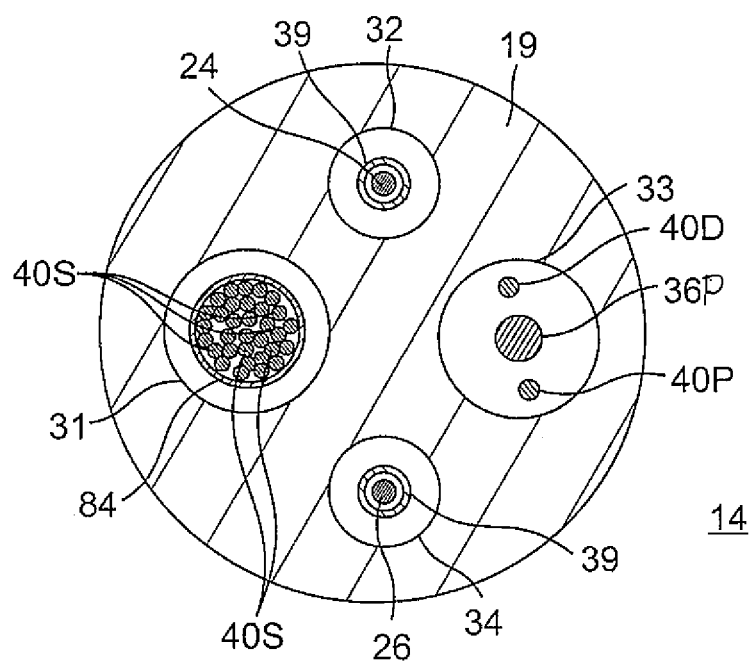
FIG. 2C is an end cross-sectional view of the deflection section of FIGS. 2A and 2B, taken along line C-C.

As shown in FIGS. 2A, 2B and 2C, the intermediate section 14 comprises a shorter section of tubing 19 having multiple lumens, for example, four off-axis lumens 31, 32, 33 and 34. The first lumen 31 carries a plurality of lead wires 40S for ring electrodes 37 carried on the spine loops 17. The second lumen 32 carries a first puller wire 24. The third lumen 33 carries a cable 36 for an electromagnetic position sensor 42 and a plurality of lead wires 40D and 40P for distal and proximal ring electrodes 38D and 38P carried on the catheter proximally of the distal electrode array 15. The fourth lumen 34 (for example, diametrically opposite of the second lumen 32 in the illustrated embodiment) carries a second puller wire 26. The tubing 19 is made of a suitable non-toxic material that is preferably more flexible than the catheter body 12. One suitable material for the tubing 19 is braided polyurethane, i.e., polyurethane with an embedded mesh of braided stainless steel or the like. The size of each lumen is not critical, but is sufficient to house the lead wires, puller wires, the cable and any other components.

The useful length of the catheter, i.e., that portion that can be inserted into the body excluding the distal electrode array 15, can vary as desired. Preferably the useful length ranges from about 110 cm to about 120 cm. The length of the intermediate section 14 is a relatively smaller portion of the useful length, and preferably ranges from about 3.5 cm to about 10 cm, more preferably from about 5 cm to about 6.5 cm.

A means for attaching the catheter body 12 to the intermediate section 14 is illustrated in FIGS. 2A and 2B. The proximal end of the intermediate section 14 comprises an outer circumferential notch 27 that receives the inner surface of the catheter body 12. The intermediate section 14 and catheter body 12 are attached by glue or the like.

If desired, a spacer (not shown) can be located within the catheter body between the distal end of the stiffening tube (if provided) and the proximal end of the intermediate section. The spacer provides a transition in flexibility at the junction of the catheter body and intermediate section, which allows this junction to bend smoothly without folding or kinking. A catheter having such a spacer is described in U.S. Pat. No. 5,964,757, the disclosure of which is incorporated herein by reference.

Figure 3A:
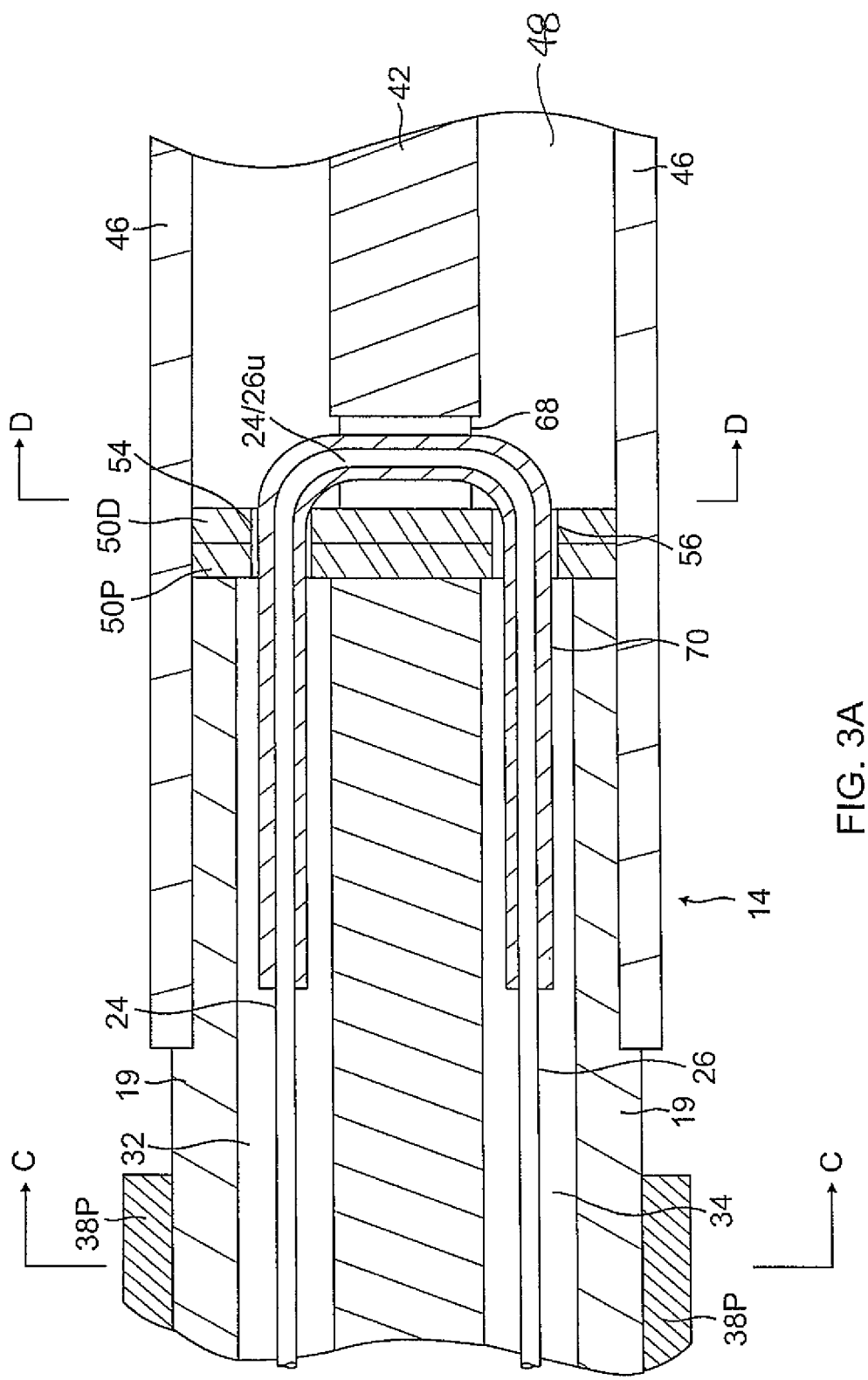
FIG. 3A is a side cross-sectional view of the catheter of FIG. 1, including a junction between the deflection section and a distal electrode assembly, taken along a first diameter.
Figure 3B:
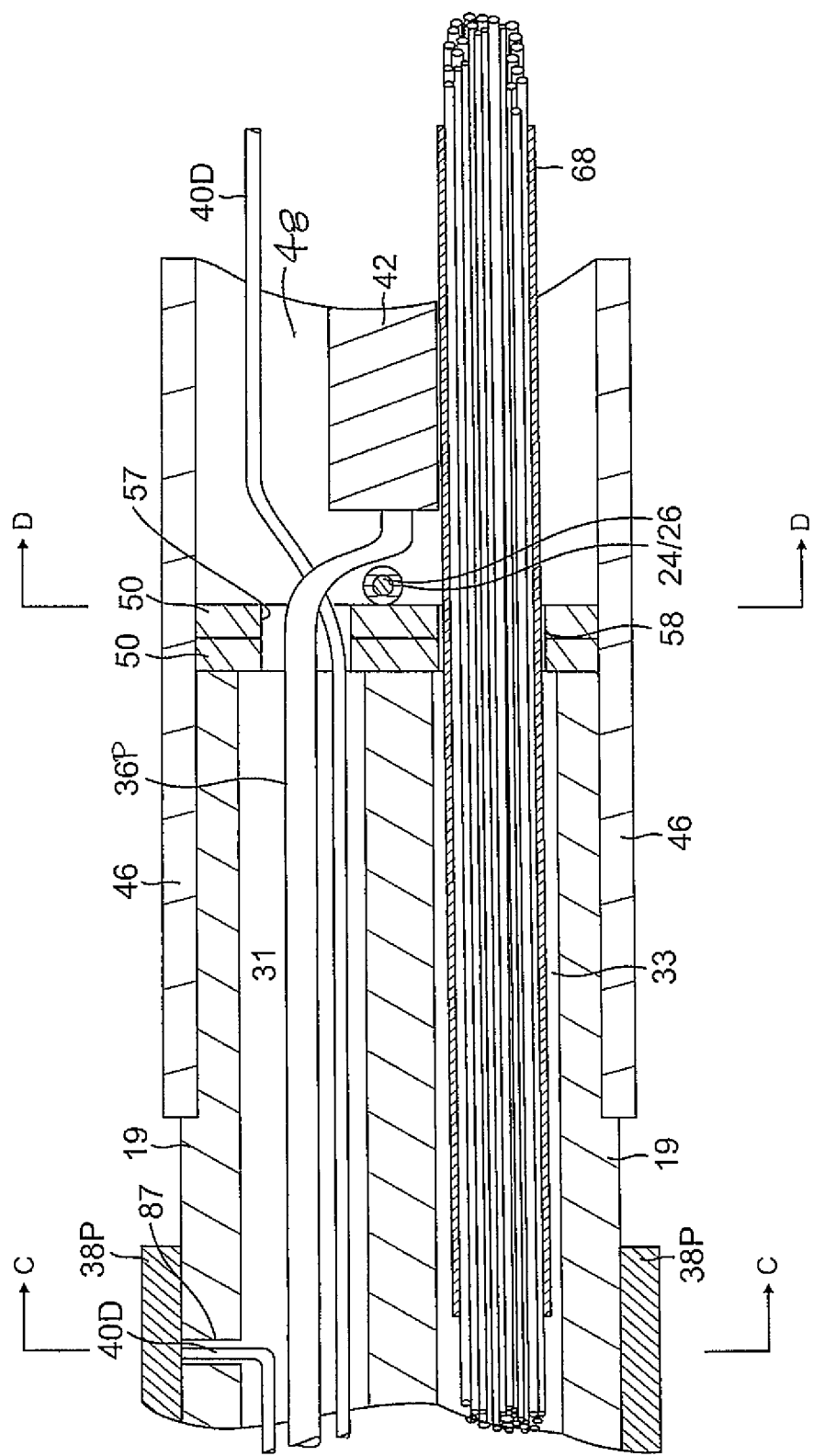
FIG. 3B is a side cross-sectional view of the junction of FIG. 3A, taken along a second diameter generally perpendicular to the first diameter.

As shown in FIGS. 3A and 3B, the distal electrode array 15 includes a mounting stem 46 in the form of a short tubing mounted on a distal end of the tubing 19 of the intermediate deflection section 14. (In that regard, it is understood that where the catheter 10 is without a deflection section 14, the mounting stem 46 is mounted on a distal end of the catheter body 12.) The stem 46 has a central lumen 48 to house various components. The intermediate section 14 and stem 46 are attached by glue or the like. The stem 46 may be constructed of any suitable material, including nitinol.

Figure 3C:
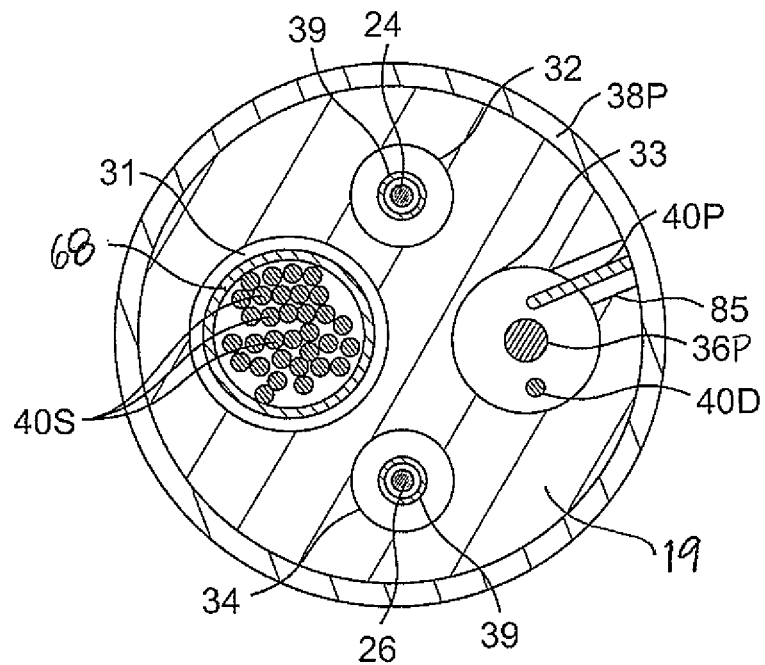
FIG. 3C is an end cross-sectional view of the deflection section of FIGS. 3A and 3B, taken along line C-C.
Figure 3D:
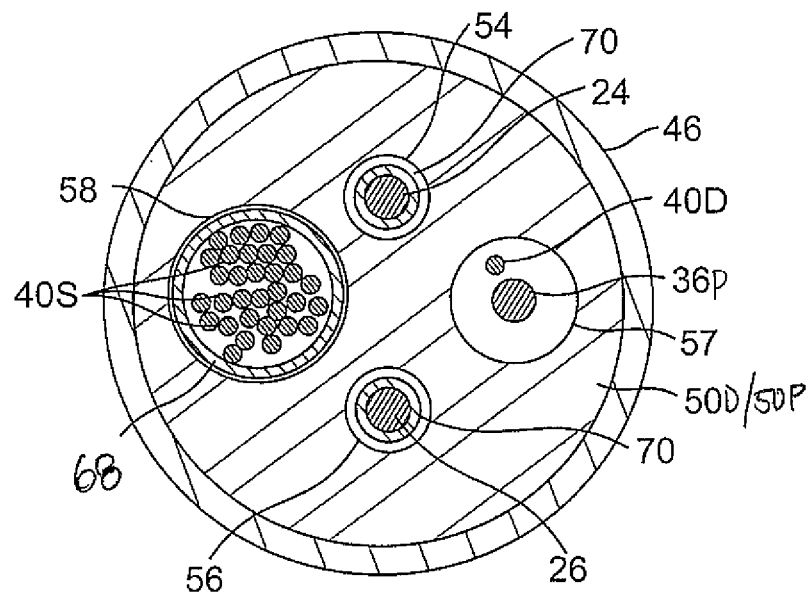
FIG. 3D is an end cross-sectional view of the junction of FIG. 3A, taken along line D-D.
Figure 4:
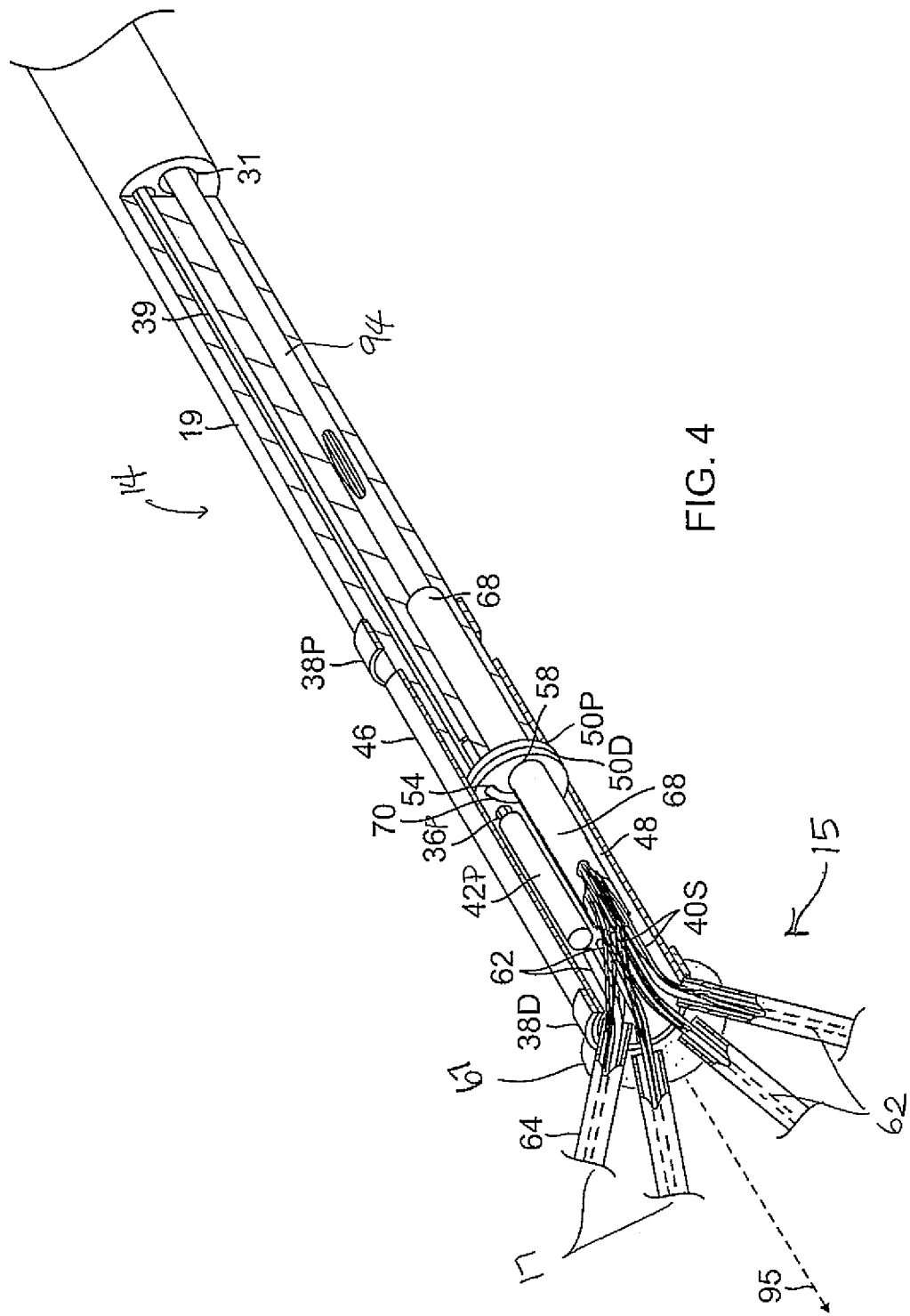
FIG. 4 is a perspective view of a junction between the deflection section and the distal electrode assembly of the catheter of FIG. 1, with parts broken away.

As shown in FIG. 4, the stem 46 houses various components, including the electromagnetic position sensor 42, and a distal anchor for the puller wires 24 and 26. In the disclosed embodiment, the distal anchor includes one or more washers, for example, a distal washer 50D and a proximal washer 50P, each of which has a plurality of matching axial through-holes that allow passage of components between the deflection section 14 and the stem 46 while maintaining axial alignment of these components relative to the longitudinal axis 95 of the catheter 10. As also shown in FIG. 3D, the through-holes include holes 54 and 56 that are axially aligned with the second and fourth lumens 32 and 34 of the tubing 19, respectively, to receive a distal end of puller wires 24 and 26, respectively. It is understood that the puller wires 24 and 26 may form a single tensile member with a distal U-bend section that passes through the holes 54 and 56. With tension on the washers 50D and 50P exerted by the U-bend section of the puller wires 24 and 26, the washers firmly and fixedly abut against the distal end of the tubing 19 of the deflection section 14 to distally anchor the U-bend section.

As also shown in FIG. 3D, each washer also includes through-hole 58 which is axially aligned with the first lumen 31 and allows passage of the lead wires 40S from the deflection section 14 and into the lumen 48 of the stem 46. Each washer further includes through-hole 57 which is axially aligned with the third lumen 33 of the tubing 19 and allows passage of the sensor cable 36 from the deflection section 14 into lumen 48 of the stem 46 where the electromagnetic position sensor 42 is housed. The lead wire 40D also passes through the hole 57 to enter the lumen 48 for attachment to the distal ring electrode 38D carried on the outer surface of the stem 46 via an opening (not shown) formed in the side wall of the stem 46 through which a distal end of the lead wire 40D is welded or otherwise attached to the distal ring electrode 38D as known in the art. Carried on the outer surface of the tubing 19 near the distal end of the intermediate deflection section 14, a proximal ring electrode 38P is connected to lead wire 40P via an opening 87 (FIG. 3B) formed in the side wall of the tubing 19 that provides communication between the third lumen 33 and outside of the tubing 19. The distal end of the lead wire is welded or otherwise attached to the proximal ring electrode 38P as known in the art.

Extending from the distal end of the stem 46 are the closed spine loops 17 of the distal electrode array 15, as shown in FIG. 5. Each spine loop has a non-conductive covering 64 that extends the exposed length of each spine loop. At the junction of distal electrode array 15 and the stem 46, the non-conductive covering 64 of each spine may be sealed at its proximal end to the stem 46 by the polyurethane 67 or the like.

In some embodiments, each spine loop 17 has a distal nonlinear connecting portion 17D, a pair of linear main electrode-carrying portions 17L, and a pair of linear proximal support portions 17P that converge into the stem 46. As shown in FIG. 7, all linear main portions (e.g., 17L1, 17L2, 17L3 and 17L4) in the array 15 lie within a common plane P ("in-plane") so as to maximum electrode-to-tissue contact. Moreover, the linear main portions 17L are arranged in a predetermined configuration within the common plane P, defined by one or more predetermined spatial relationships with each other, as maintained by the distal portions 17D of the loops which connect corresponding pairs of main portions 17L at their distal ends. In that regard, the distal portions 17D are angled out of the common plane P ("off-plane") so that the distal portions 17D are free from contact with each other and are thus noninterfering with the linear main portions 17L remaining in-plane. The distal portions 17D are nonlinear, and may assume any curved or angular shape, for example, triangular (FIG. 8) or rectangular (FIG. 9).

In the illustrated embodiment of FIG. 7, a first distal portion 17D1 is angled out of plane in one direction (e.g., upwardly) and a second distal portion 17D2 is angled out of plane in an opposite direction (e.g., downwardly). Furthermore, a third spine loop 17D3 is angled out of plane in the one direction (e.g., upwardly) and a fourth spine loop 17D4 is angled out of plane in the opposite direction (e.g., downwardly). As such, adjacent pair distal portions 17D1 and 17D2 are angled oppositely of each other, as well as adjacent pair distal portions 17D2 and 17D3, and similarly adjacent pair distal portions 17D3 and 17D4. The off-plane angle θ may range between about 1 and 45 degrees from the common plane, and preferably between about 5 and 20 degrees, and more preferably be about 10 degrees.

Moreover, to maximize electrode density of the array 15 and efficiency of each linear main portion 17L as an electrode-carrying portion, the spine loops 17 are in a laterally offset arrangement where at least one linear main portion 17L of each spine loop is positioned between linear main portions 17L of one or more different spine loop. Or, in other words, each pair of linear main portions 17L of a spine loop is separated therebetween by at least a linear main portion 17L of a different spine loop. As such, the array 15 is able to provide greater electrode density yet remain of a more simplistic construction where the electrode-carrying linear main portions 17L of each spine loop extend in-plane as supported by the noninterfering distal portions 17D.

In the illustrated embodiment of FIG. 7, the spine loops are laterally offset. For example, at least one linear portion 17L1 is positioned between linear portions 17L2. Moreover, for example, the pair of linear portions 17L3 is separated therebetween by the linear portion 17L4.

Predetermined configuration within the common plane P may include one or more predetermined spatial relationships between the spine loops or portions thereof. One or more spatial relationships may be defined by spacing S between adjacent linear main portions 17L along the length of the array, for example, proximal spacing SP and distal spacing SD, as shown in FIG. 5. Predetermined spatial relationships may also include predetermined spacing d between the ring electrodes 37 carried on the linear main portions 17L. In the illustrated embodiment of FIG. 5, the linear main portions 17L are parallel with each other such that proximal spacings SPi and distal spacings SDi are equal between pairs of adjacent linear main portions 17L. For example, where spacing SPi, SDi are uniform to each other and throughout the array 15, and spacing d is uniform throughout the array 15, the array 15 is configured to support the electrodes in a grid-like pattern, as shown in FIG. 5. It is understood that the spacings SPi and SDi may be varied throughout the array, as desired or appropriate, to provide different configurations.

For anchoring a proximal end of the array 15 in the stem 46, the proximal portions 17P of the spine loops can be configured, as desired or appropriate, to support the linear main portions 17L in-plane, for example, in equi-angular distribution around a center of the stem. In the illustrated embodiment of FIG. 5, the four proximal portions 17P are potted in four quadrants about the center longitudinal axis 46A of the stem 46.

The plurality of loops may range between about 2 and 4. Each spine loop may have a exposed linear length ranging between about 5 and 50 mm, preferably about 10 and 35 mm, and more preferably about 28 mm. The array may have dimensions of about 1.5 cm×1.0 cm The spacing SP and SD between adjacent linear main portions 17L each may range between about 1 mm and 20 mm, preferably about 2 and 10 mm, and more preferably about 4 mm. The spacing d between electrodes ranges between about 0.5 mm-12 mm. The surface area of the array 15 may range between about 1.5 cm$^2$ to 3.0 cm$^2$, preferably between about 1.9 cm$^2$ and 2.5 cm$^2$, and more preferably about 2.2 cm$^2$ As shown in FIG. 4, each spine loop 17 has an elongated shape-memory support member 62 extending through the length of the loop. A proximal portion of each member 62 extends into a distal end portion of the stem 46 and is anchored in the lumen 48 of the stem 46. Each spine loop 17 has a nonconductive tubing or covering 64 that covers the shape-memory member 62 and the plurality of ring electrode 37 carried on each linear main portion 17L may range between about 6 and 12, preferably about 6 and 9, and more preferably about 8. Accordingly, the distal electrode array 15 carries a plurality of electrodes ranging between about 20 and 72, preferably between about 28 and 36 electrodes, and more preferably about 32 electrodes. In some embodiments, the electrode density is about 15 electrodes per square centimeter and dimensions of about 12 mm×18 mm.

The shape-support support member 62 is made of a material having shape-memory, i.e., that can be temporarily straightened or bent out of its original shape upon exertion of a force and is capable of substantially returning to its original shape in the absence or removal of the force. One suitable material for the support member is a nickel/titanium alloy. Such alloys typically comprise about 55% nickel and 45% titanium, but may comprise from about 54% to about 57% nickel with the balance being titanium. A nickel/titanium alloy is nitinol, which has excellent shape memory, together with ductility, strength, corrosion resistance, electrical resistivity and temperature stability. The non-conductive covering 64 can be made of any suitable material, and is preferably made of a biocompatible plastic such as polyurethane or PEBAX. If desired, the support member 62 can be eliminated and the distal end of the non-conductive covering 64 can be pre-formed to have the desired curvature or configuration.

Each shape-memory support member 62 extending through its respective nonconductive covering 64 has a proximal end that is received and anchored in the stem 46 by polyurethane 67 or the like. Lead wires 40S for the spine electrodes 37 extend through a protective polytube 68, as shown in FIG. 4. The lead wires 40S diverge at the distal end of the polytube 68, and extend toward their respective shape-memory support member 62, into their respective nonconductive covering 64 of their respective spines. As shown in FIG. 5C, each lead wire 40S is connected to its respective ring electrode 37 on the spine loop 17 via a respective opening 69 formed in the side wall of the covering 64 through which a distal end of the lead wire reaches outside of the covering 64 and is welded or otherwise attached to its ring electrode 37.

In other embodiments, irrigated ring electrodes 37I are carried on the spine loops 17, as shown in FIGS. 6, 6A and 6B. The spines forming the loops 17 include a multi-lumened tubing 80 having, for example, multiple lumens, including a first lumen 81 for the shape-memory member 62, a second lumen 82 for lead wires 40S, and a third lumen 83 for passing irrigation fluid via a passage 88 formed in the sidewall of the tubing 80 to annular space gap G between outer wall of the tubing 80 and side wall of the ring electrode 37I which are formed with fluid ports 85. A fourth lumen 84 may be provided to pass cable 36D for distal electromagnetic position sensor 42D (not shown).

The proximal ends of the lead wires 40S, 40D and 40P for the spine loop ring electrodes 37 and for the distal and proximal ring electrodes 38D and 38P, respectively, are electrically connected to a suitable connector (not shown) in the distal end of the control handle 16, which is connected to a source of ablation energy, e.g., RF energy, as is known in the art. The lead wires 40S, 40D and 40P extend through the central lumen 18 of the catheter body 12 (FIG. 2B). The lead wires 40S extend through the first lumen 31 of the tubing 19 of the intermediate section 14, and the lead wires 40D and 40P extend through the third lumen 33 of the tubing 19 (FIGS. 2C and 3C). Passing through the holes 58 in the washers 50D and 50P, the lead wires 40S extend through the polytube 68 which protects them from being damaged by the hole 58 (FIGS. 3D and 4).

In the depicted embodiment, the lead wires 40S extending through the central lumen 18 of the catheter body 12 and the first lumen 31 in the deflection section 14 may be enclosed within a protective sheath 94 to prevent contact with other components in the catheter. The protective sheath can be made of any suitable material, preferably polyimide. As would be recognized by one skilled in the art, the protective sheath can be eliminated if desired.

The ring electrodes 37, 37I and 38D and 38P can be made of any suitable solid conductive material, such as platinum or gold, preferably a combination of platinum and iridium, and mounted onto the non-conductive cover 64, the stem 46 and or the tubing 19 with glue or the like. Alternatively, the ring electrodes can be formed by coating the non-conductive cover 64, the stem 46 and/or the tubing 19 with an electrically conducting material, like platinum, gold and/or iridium. The coating can be applied using sputtering, ion beam deposition or an equivalent technique.

In some embodiments, each ring electrode is relatively short, having a length ranging from about 0.4 mm to about 0.75 mm. The electrodes may also be arranged in pairs, where two electrodes of a pair are spaced more closely to each other than they are to other pairs of electrodes. The closely-spaced electrode pairs allow for more accurate detection of near field pulmonary vein potential versus far field atrial signals, which is very useful when trying to treat atrial fibrillation. Specifically, the near field pulmonary vein potentials are very small signals whereas the atria, located very close to the pulmonary vein, provides much larger signals. Accordingly, even when the mapping array is placed in the region of a pulmonary vein, it can be difficult for the physician to determine whether the signal is a small, close potential (from the pulmonary vein) or a larger, farther potential (from the atria). Closely-spaced bipole electrodes permit the physician to more accurately determine whether he is looking at a close signal or a far signal. Accordingly, by having closely-spaced electrodes, one is able to target exactly the locations of myocardial tissue that have pulmonary vein potentials and therefore allows the clinician to deliver therapy to the specific tissue. Moreover, the closely-spaced electrodes allow the physician to determine the exact anatomical location of the ostium/ostia by the electrical signal.

In some embodiments, the proximal electromagnetic position sensor 42P is housed in the lumen of the stem (FIG. 4). A sensor cable 36P extends from a proximal end of the position sensor 42P, and through the hole 57 of the washers 50 (FIG. 3D), the third lumen 33 of the tubing 19 of the deflection section 14 (FIG. 2C), and the central lumen 18 of the catheter body 12 (FIG. 2B). The cable 36P is attached to a PC board in the control handle 16, as known in the art. In some embodiments, one or more distal electromagnetic position sensors may be housed in the array, for example, in one or more distal portions of the array. Sensor cables 36D may extend through the spine covering 64 (FIG. 5C) or the lumen 84 of the tubing 80 (FIG. 6B).

As shown in FIGS. 2A and 2C, the puller wires 24 and 26 (whether as two separate tensile members or parts of a single tensile member) are provided for bi-directional deflection of the intermediate section 14. The puller wires 24 and 26 are actuated by mechanisms in the control handle 16 that are responsive to a thumb control knob or a deflection control knob 11. Suitable control handles are disclosed in U.S. Pat. Nos. 6,123,699; 6,171,277; 6,183,435; 6,183,463; 6,198,974; 6,210,407 and 6,267,746, the entire disclosures of which are incorporated herein by reference.

The puller wires 24 and 26 extend through the central lumen 18 of the catheter body 12 (FIG. 2A) and through the second and fourth lumens 32 and 34, respectively, of the tubing 19 of the deflection section 14 (FIG. 2C). As shown in FIGS. 3A and 3C, they extend through holes 54 and 56, respectively of the washers 50. Where the puller wires are part of a single tensile member, the single tensile member has a U-bend 24/26U (FIG. 3A) at the distal face of the distal washer 50D which anchors the distal ends of the puller wires. In that regard, the U-bend extends through a short protective tubing 70 to protect the puller wires from the holes 54 and 56. Alternatively, where the puller wires are separate tensile members, their distal ends may be anchored via T-bars, as known in the art and described in, for example, U.S. Pat. No. 8,603,069, the entire content of which is incorporated herein by reference. In any case, the puller wires 24 and 26 are made of any suitable metal, such as stainless steel or Nitinol, and each is preferably coated with TEFLON or the like. The coating imparts lubricity to the puller wires. The puller wires preferably have a diameter ranging from about 0.006 to about 0.010 inch.

A compression coil 66 is situated within the central lumen 18 of the catheter body 12 in surrounding relation to each puller wire 24, as shown in FIG. 2B. Each compression coil 66 extends from the proximal end of the catheter body 12 to the proximal end of the intermediate section 14. The compression coils 66 are made of any suitable metal, preferably stainless steel. Each compression coil 66 is tightly wound on itself to provide flexibility, i.e., bending, but to resist compression. The inner diameter of the compression coil 66 is preferably slightly larger than the diameter of its puller wire. The Teflon coating on each puller wire allows it to slide freely within its compression coil.

The compression coil 66 is anchored at its proximal end to the outer wall 20 of the catheter body 12 by a proximal glue joint (not shown) and at its distal end to the intermediate section 14 by a distal glue joint 92. Both glue joints may comprise polyurethane glue or the like. The glue may be applied by means of a syringe or the like through a hole made the sidewalls of the catheter body 12 and the tubing 19. Such a hole may be formed, for example, by a needle or the like that punctures the sidewalls which are heated sufficiently to form a permanent hole. The glue is then introduced through the hole to the outer surface of the compression coil 66 and wicks around the outer circumference to form a glue joint about the entire circumference of the compression coil.

Within the second and fourth lumens 32 and 34 of the intermediate section 14, each puller wire 24 and 26 extends through a plastic, preferably Teflon, puller wire sheath 39 (FIGS. 2A and 2C), which prevents the puller wires from cutting into the sidewall of the tubing 19 of the deflection section 14 when the deflection section 14 is deflected.

In use, a suitable guiding sheath (not shown) is inserted into the patient with its distal end positioned at or near a desired tissue location for diagnostics such as mapping and/or treatment such as ablation. An example of a suitable guiding sheath for use in connection with the present invention is the Preface Braided Guiding Sheath, commercially available from Biosense Webster, Inc. (Diamond Bar, Calif.). The catheter 10 is passed through the guiding sheath and advanced therethrough to the desired tissue location. In particular, the spine loops 17 of the distal electrode array 15 fed into the proximal end of the guiding sheath. After the distal electrode array 15 has reached the desired tissue location, the guiding sheath is pulled proximally, exposing at least the array. Outside of the guiding sheath 36, the linear main portions 17L of the spine loops extend generally in a common plane, as shown in FIG. 5, as supported by the noninterfering angled distal portions 17D. The distal portions 17D connecting the linear main portions 17L prevent the latter from spreading, diverging and/or going out of plane.

Figure 10:
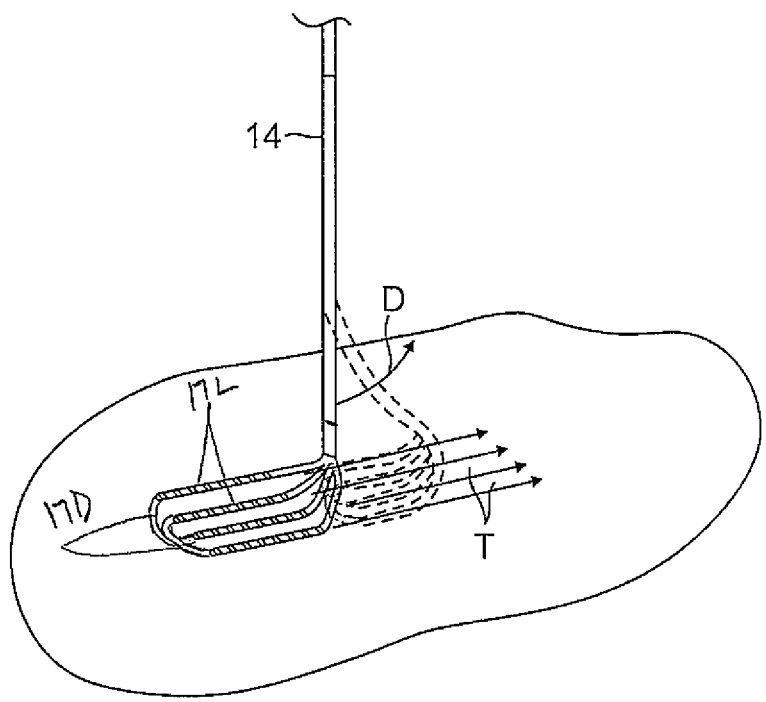
FIG. 10 is a schematic drawing illustrating a method of using the catheter of the present invention, according to one embodiment.

The array 15 has a first side and a second side. As shown in FIG. 10, the user places the first side against the tissue surface, with at least the intermediate section 14 (if not also a distal portion of the catheter body 12) generally perpendicular to the tissue surface, and actuates the control handle to deflect the intermediate deflection section 14 (arrow D) such that the first side deflects toward the catheter, which drags the first side of the linear main portions 17L across the tissue surface as the section 14 is deflecting. The linear main portions 17L are dragged across the tissue surface while remaining generally parallel to each other (as maintained by the distal portions 17D) along tracks T which are generally linear and parallel, and in the same direction as the deflection direction D.

Figure 11:
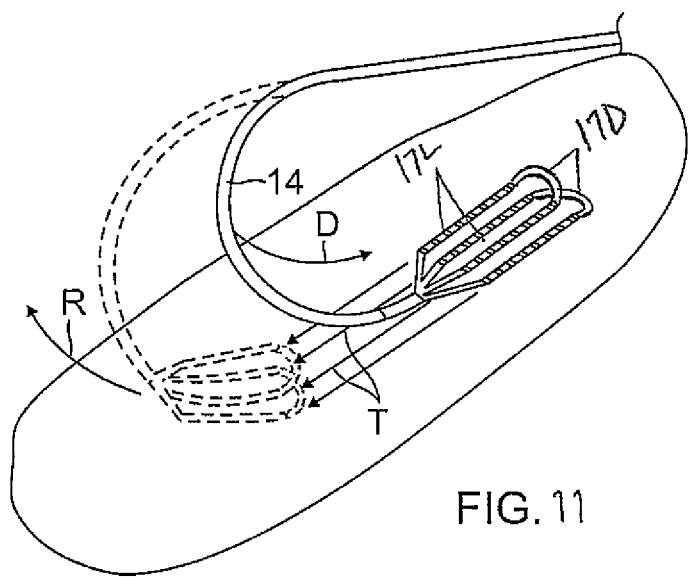
FIG. 11 is a schematic drawing illustrating a method of using the catheter of the present invention, according to another embodiment.

Alternatively, as shown in FIG. 11, the user actuates the control handle to deflect the section 14 along direction D with the first surface of the array 15 deflected toward the catheter. The user then positions at least the distal portion of the catheter body 12 generally parallel with the tissue surface and places the second surface of the array 15 against the tissue surface. The user then releases the deflection (along opposite direction R) which drags the second surface of the linear main portions 17L across the tissue surface as the deflection section 14 straightens. The linear main portions 17L are dragged across the tissue surface while remaining generally parallel to each other (as maintained by the distal portions 17D) along tracks T which are generally linear and parallel, and in the direction R opposite to the deflection direction D.

In either manner, the spine electrodes 37 are carried in-plane on the linear main portions 17L for maximizing contact with the tissue surface while the linear main portions 17L generally maintain a consistent separation spacing from each other as the spine loops are dragged across the tissue surface for high density electrode sensing and uniform and predictable mapping. By keeping the linear main portions 17L separated, they are less prone to overlap and the electrodes 37 are less susceptible to "cross talk" or electromagnetic interference that can arise when two electrodes are in overly close proximity or contact. In accordance with a feature of the invention, the array has an "n×m" electrode layout or arrangement, for example, four spines, with eight electrodes on each spine, for a total of 32 closely-spaced ring electrodes 37 for mapping.

In some embodiments, the distal electrode array 15 includes a spacer member 86, e.g., a bar or bracket that extends between at least two spines to mechanically restrain them and keep them in a predetermined spatial relationship. The spacer member can be configured to restrain movement in one or more directions while allowing movement in other directions. In the illustrated embodiment of FIG. 5, the spacer member 86 extends between linear portions 17L, fixed at their ends to the linear portions 17L by adhesive, e.g. polyurethane, although it is understand that the spacer member may extend between any two or more of the same and/or different portions of the spine loops 17, as desired or appropriate. Regions of the spine loops may also be heat bonded or melted together as desired or appropriate.

In some embodiments, the ring electrodes 38D and 38P proximal of the array 15 serve as reference electrodes for visualization of the catheter on a 3-D mapping system, such as CARTO® 3 SYSTEM available from Biosense Webster, Inc., which automatically locates the EM sensor 42, processes reference location values from electrodes 38D and 38P, which are at a constant location from the EM sensor(s) and determines the location of the electrodes 37 and 37I and visualizes the remainder of the electrode array 15.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale. Also, different features of different embodiments may be combined as needed or appropriate. Moreover, the catheters described herein may be configured to apply various energy forms, including microwave, laser, RF and/or cryogens. Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter comprising:
an elongated catheter body having a distal end;
a distal electrode array mounted on the distal end of the catheter body, the distal electrode array comprising a plurality of offset spine loops, each spine loop having at least a pair of electrode-carrying portions and a distal portion connecting the pair of electrode-carrying portions, wherein the electrode-carrying portions of the plurality of offset spine loops lie in a single common plane, and the distal portions of the plurality of offset spine loops are angled out of the single common plane; and
at least one ring electrode disposed upon each electrode-carrying portion,
wherein at least one of the ring electrodes comprises an irrigated ring electrode and
wherein each spine loop includes at least one lumen therethrough.

2. The catheter of claim 1, wherein the at least one lumen includes a first lumen containing a shape-memory member, a second lumen containing a lead wire, a third lumen adapted to be connected to a source of an irrigation fluid, and a fourth lumen containing a position sensor.

3. The catheter of claim 2, wherein the catheter body includes an intermediate section having multiple lumens.

4. The catheter of claim 3, wherein the multiple lumens comprise off-axis lumens.

5. The catheter of claim 3, wherein the multiple lumens comprise a fifth lumen containing a lead wire, a sixth lumen containing a first puller wire, a seventh lumen containing an electromagnetic sensor, and an eighth lumen containing a second puller wire.

6. The catheter of claim 3, further comprising a spacer member extending between at least two of the electrode-carrying portions.

7. The catheter of claim 6, wherein the electrode-carrying portions comprise linear portions.

8. A catheter comprising:
an elongated catheter body having a distal end;
a distal electrode array mounted on the distal end of the catheter body, the distal electrode array comprising a plurality of offset spine loops, each spine loop having at least a pair of electrode-carrying portions and a distal portion connecting the pair of electrode-carrying portions, wherein the electrode-carrying portions of the plurality of offset spine loops lie in a single common plane, and the distal portions of the plurality of offset spine loops are angled out of the single common plane;
at least one irrigated ring electrode disposed upon each electrode-carrying portion; and
a spacer member extending between at least two of the electrode-carrying portions.

9. The catheter of claim 8, wherein the at least two of the electrode-carrying portions comprises a first electrode-carrying portion of a first spine loop and a second electrode-carrying portion of a different spine loop.

10. The catheter of claim 8, wherein the spacer member includes a bar.

11. The catheter of claim 8, wherein the spacer member includes a bracket.

12. The catheter of claim 8, wherein the spacer member comprises a member affixed to the at least two of the electrode-carrying portions.

13. The catheter of claim 12, wherein each spine loop includes at least one lumen therethrough.

14. The catheter of claim 13, wherein the at least one lumen includes a first lumen containing a shape-memory member, a second lumen containing a lead wire, a third lumen adapted to be connected to a source of irrigation fluid, and a fourth lumen containing a position sensor.

15. The catheter of claim 14, wherein the catheter body includes an intermediate section having multiple lumens.

16. The catheter of claim 15, wherein the multiple lumens comprise off-axis lumens.

17. The catheter of claim 16, wherein the multiple lumens comprise a fifth lumen containing a lead wire, a sixth lumen containing a first puller wire, a seventh lumen containing an electromagnetic sensor, and an eighth lumen containing a second puller wire.

18. The catheter of claim 15, wherein the electrode-carrying portions each comprise a linear portion.

* * * * *